(12) United States Patent
Ke et al.

(10) Patent No.: US 11,278,584 B2
(45) Date of Patent: *Mar. 22, 2022

(54) PHARMACEUTICAL COMPOSITION FOR PREVENTING AND TREATING SENILE DEMENTIA AND PREPARATION METHOD THEREOF

(71) Applicant: SICHUAN JISHENGTANG PHARMACEUTICAL CO., LTD., Sichuan (CN)

(72) Inventors: Xiao Ke, Sichuan (CN); Xiaofeng Hao, Sichuan (CN); Baohua Meng, Sichuan (CN)

(73) Assignee: SICHUAN JISHENGTANG PHARMACEUTICAL CC, Sichuan (CN)

( * ) Notice: Subject to any disclaimer, the term of this patent is extended or adjusted under 35 U.S.C. 154(b) by 58 days.

This patent is subject to a terminal disclaimer.

(21) Appl. No.: 16/830,575

(22) Filed: Mar. 26, 2020

(65) Prior Publication Data

US 2020/0222491 A1    Jul. 16, 2020

Related U.S. Application Data

(63) Continuation of application No. 15/319,346, filed as application No. PCT/CN2015/081950 on Jun. 19, 2015, now Pat. No. 10,646,536.

(30) Foreign Application Priority Data

Jun. 20, 2014 (CN) .......................... 201410280231.2

(51) Int. Cl.
| | | |
|---|---|---|
| *A61K 36/8964* | (2006.01) | |
| *A61K 36/076* | (2006.01) | |
| *A61K 36/254* | (2006.01) | |
| *A61K 36/296* | (2006.01) | |
| *A61K 9/16* | (2006.01) | |

(52) U.S. Cl.
CPC ............ *A61K 36/8964* (2013.01); *A61K 9/16* (2013.01); *A61K 36/076* (2013.01); *A61K 36/254* (2013.01); *A61K 36/296* (2013.01); *A61K 2236/331* (2013.01); *A61K 2236/333* (2013.01); *A61K 2236/37* (2013.01); *A61K 2236/39* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 10,646,536 | B2 * | 5/2020 | Ke ..................... | A61K 36/8964 |
| 2004/0185128 | A1 | 9/2004 | Kim et al. | |
| 2017/0136083 | A1 | 5/2017 | Ke et al. | |

FOREIGN PATENT DOCUMENTS

| | | |
|---|---|---|
| CN | 1198336 A | 11/1998 |
| CN | 1857666 A | 11/2006 |
| CN | 101229293 A | 7/2008 |
| CN | 101417048 A | 4/2009 |
| CN | 101543576 A | 9/2009 |
| CN | 101574499 A | 11/2009 |
| CN | 101732660 A | 6/2010 |
| CN | 101940703 A | 1/2011 |
| CN | 102698172 A | 10/2012 |
| CN | 103099833 A | 5/2013 |
| EP | 3159004 A1 | 4/2017 |
| JP | 2012126716 A | 7/2012 |
| WO | 02/102397 A1 | 12/2002 |
| WO | 2004/011719 A1 | 2/2004 |
| WO | 2015192804 A1 | 12/2015 |

OTHER PUBLICATIONS

Wang et al., "Compatibility art of traditional Chinese medicine: From the perspective of herb pairs", Journal of Ethnopharmacology 143 (2012), pp. 412-423.
Jia et al., "Letter To The Editor, The Rediscovery of Ancient Chinese Herbal Formulas", Phytotherapy Research, Phytother. Res. 18, (2004), pp. 681-686.
Author Unknown, Chinese Office Action and Search Report dated Aug. 1, 2018, CN Application No. 201510345653.8, filed Jun. 19, 2015, pp. 1-9 (including English translation).
Hu et al., "A new approach to the pharmacological regulation of memory: sarsasapogenin improves memory by elevating the low muscarinic acetylcholine receptor density in brains of memory-deficit rat models", Word Science and Technology/ Modernization of Traditional Chinese Medicine and Materia Medica, vol. 9, No. 2, Dec. 31, 2007, pp. 1-7 (English translation not provided).
V.G. Galkovskaya (Deputy Chief), Notice of Allowance dated Sep. 5, 208, RU Application No. 2016146370/15(074426), filed Jun. 19, 2015, pp. 1-24 (including English translation).
Korean Office Action dated Sep. 19, 2018, KR Application No. 10-2018-7021909, pp. 1-14 (including English translation).

(Continued)

*Primary Examiner* — Susan Hoffman

(74) *Attorney, Agent, or Firm* — MH2 Technology Law Group LLP

(57) ABSTRACT

The present disclosure relates to a pharmaceutical composition for preventing and treating senile dementia and preparation method thereof. The active ingredients of the pharmaceutical composition are prepared from raw medicinal materials comprising 20-50 parts by weight of Epimedii Folium and 15-55 parts by weight of Poria; or from raw medicinal materials comprising 20-50 parts by weight of Epimedii Folium, 15-55 parts by weight of Poria and 10-55 parts by weight of Acanthopanax, or from raw medicinal materials comprising 20-50 parts by weight of Epimedii Folium, 15-50 parts by weight of Poria, 15-50 parts by weight of Acanthopanax and 6-15 parts by weight of Anemarrhenae Rhizoma.

11 Claims, No Drawings

(56) References Cited

OTHER PUBLICATIONS

Jandae27 (Author), Epimedium koreanum NAKAI-Epimedium Herb, This blog is about Epimedium Herb and its effects., https://blog.naver.com/jandae27/40049553352, pp. 1-12 (English translation not provided), 2008.

Extended European Search Report dated Jan. 19, 2018, EP Application No. 15810456.2, pp. 1-12.

Second Office Action dated Jan. 29, 2018, RU Application No. 2016146370, pp. 1-17 (including English translation).

Zhihong Lin et al., "Traditional Chinese Medicine for Senile Dementia", Evidence-Based Complimentary and Alternative Medicine, vol. 2012, Article ID 692621, doi:10.1155/2012/692621, pp. 1-14.

Jin Lu et al., "Effect of Acanthopanax Senticocous Saponins on Microvessel Density(MVD)and VEGF of Cerebral Tissue of Vascular Dementia in Rats", Chinese Archives of Traditional Chinese Medicine, Jun. 2013, pp. 1-2.

Han Yan et al., "Treating senile dementia with traditional Chinese medicine", Clinical Interventions in Aging 2007:2(2), pp. 201-208.

Australian Examination Report dated Aug. 21, 2017, Australian Application No. 2015276657, pp. 1-11.

Japanese Office Action dated Aug. 29, 2017, Japanese Application No. 2017-513303, pp. 1-9 (including English translation).

Author Unknown, 岐阜県森林科学研究所業務報告 Report of Gifu Prefecture Forestry Research Institute, 2004, vol. 2004, p. 43-50, (plus one page English translation of description only).

Author Unknown, Korean Office Action dated Oct. 18, 2017, Korean Application No. 10-2016-7035567, pp. 1-12 (including English translation).

Russian Office Action dated Oct. 2, 2017, Russian Application No. 2016146370/15, pp. 1-17 (including English translation).

Canadian Office Action dated Jun. 20, 2017, Canadian Application No. 2,950,638, pp. 1-5.

Jenefer Alam (DR) (Authorized Officer), Singapore Written Opinion dated Feb. 17, 2017, Singapore Application No. 11201609701U, filed Jun. 19, 2015, pp. 1-5.

Author Unknown, International Search Report dated Sep. 9, 2015, International Application No. PCT/CN2015/081950, filed Jun. 19, 2015, pp. 1-12.

\* cited by examiner

PHARMACEUTICAL COMPOSITION FOR PREVENTING AND TREATING SENILE DEMENTIA AND PREPARATION METHOD THEREOF

CROSS-REFERENCE TO RELATED APPLICATION(S)

This application is a continuation of U.S. Patent Application No. 15/319,346, filed on Dec. 15, 2016, now U.S. Pat. No. 10,646,536, which is a national phase application of International Application No. PCT/CN2015/081950, filed on Jun. 19, 2015. The International Application claims priority to Chinese Patent Application No. 201410280231.2, filed on Jun. 20, 2014. The aforementioned patent applications are hereby incorporated by reference in their entireties.

TECHNICAL FIELD

The present disclosure relates to pharmaceutical fields, and in particular to a pharmaceutical composition for preventing and treating senile dementia and preparation method thereof.

BACKGROUND

With accelerating of stepping into an aging society throughout the world, various gerontal neurodegenerative diseases, such as mild cognitive impairment, senile dementia and the like, have become major risk factors that threaten human health in later life and decrease life quality of old people, which brings about serious economic burden and heavy psychological pressure to the society and families Senile dementia can be divided into Alzheimer's disease (AD), vascular dementia, and a mixed dementia that the aforementioned two diseases coexist. Senile dementia is a primary degenerative brain disease occurring in or at the early stage of the geratic period, and is a persistent dysfunction of higher-order nervous activities. Clinically, it is manifested as worsening of cognitive and memory functions, progressive deterioration of daily life ability, as well as various symptoms such as neuropsychiatric symptoms and behavior dysfunction. Senile dementia is a disease with relatively high incidence, and the data of the World Health Organization shows that currently there are approximately 20 million older people suffering from senile dementia throughout the world, and it would be expected that by 2020 there will be more than 30 million patients suffering from senile dementia throughout the world. Therefore, it is a research emphasis for medical workers of different countries throughout the world to develop a drug for improving cognition impairment and treating senile dementia, which gains great attention from Chinese and western medical professions.

Currently, drugs used for treating senile dementia mainly include an acetylcholinesterase (AchE) inhibitor, an anti-immune-inflammation drug, a calcium ion antagonist, an antioxidant and the like. Such drugs approved by the Food and Drug Administration (FDA) (US) include donepezil, galanthamine, nimodipine, memantine hydrochloride and the like. These drugs can only temporarily relieve the deterioration of cognitive functions of the patients, but cannot suspend the progression of diseases.

Furthermore, some of the aforementioned drugs have adverse effects such as serious liver and kidney toxicities, and some of the aforementioned drugs are too expensive to be afforded by the patients and family members thereof.

Thus, it still needs to develop a new drug with a good therapeutic effect, little toxic and side effects and an appropriate price. Recently, specialists and scholars from China and abroad turn their attention to traditional Chinese medicines and natural medicines, and attempt to conduct a research on treatment of senile dementia. The modern traditional Chinese medicine (TCM) believes that, senile dementia is a common gerontal disease characterized by deficiency in origin and excess in superficiality, wherein the deficiency in origin is mainly caused by deficiency of the kidney essence, deficiency of marrow sea, and failure of lucid yang to rise; kidney deficiency is the root cause of senile dementia, and malnutrition of internal organs is closely related to the incidence of senile dementia. Therefore senile dementia is often treated by tonifying Kidney and strengthening essence.

As recorded in Encyclopedia of Chinese herbal medicine, Poria has effects of removing dampness and promoting diuresis, and calming the heart and strengthening the spleen, which can be used to treat edema and oliguria, dizziness and palpitation due to fluid retention, deficiency of the spleen and lack of appetite, loose stool or diarrhoea, malaise, and palpitation due to fear and insomnia. Acanthopanacis Senticosi Radix et Rhizoma seu Caulis (also known as "Acanthopanax") has effects of invigorating qi and strengthening the spleen, and tonifying kidney and calming nerves, which is used to treat Yang deficiency of both spleen and kidney, debilitation and hypodynamia, loss of appetite, waist and knee pain, and insomnia and dreaminess. Epimedii Folium (also known as "Epimedium")has effects of invigorating kidney and strengthening Yang; dispelling wind and eliminating dampness; strengthening muscles and bones, which is mainly used to treat impotence and spermatorrhea, deficient-cold-type infertility, frequent micturition and incontinence, kidney deficiency and cough with asthma, soreness and weakness of waist and knees, rheumatic arthralgia, hemiplegia, and insensitivity of the limbs. Anemarrhenae Rhizoma has effects of clearing away heat and purging pathogenic fire, nourishing Yin and moistening dryness, and quenching thirst and relieving restlessness, which may be used to treat warm febrile diseases; high fever and polydipsia; cough or asthma; cough caused by dryness; constipation; osteopyrexia and fever; dysphoria and insomnia; and diabetes and stranguria with turbid discharge.

SUMMARY

The present disclosure in one aspect provides a pharmaceutical composition for treating or preventing senile dementia, the active ingredients of which are prepared from raw medicinal materials comprising 20-50 parts by weight of Epimedium (i.e. Epimedii Folium) and 15-55 parts by weight of Poria.

The present disclosure in another aspect provides a pharmaceutical composition for treating or preventing senile dementia, the active ingredients of which are prepared from raw medicinal materials comprising 20-50 parts by weight of Epimedium, 15-55 parts by weight of Poria and 10-55 parts by weight of Acanthopanax, preferably from traditional Chinese medicinal materials comprising 20-30 parts by weight of Epimedium, 20-45 parts by weight of Poria and 20-55 parts by weight of Acanthopanax, more preferably from traditional Chinese medicinal materials comprising 30 parts by weight of Epimedium, 30 parts by weight of Poria and 35 parts by weight of Acanthopanax.

The present disclosure in a further aspect provides a pharmaceutical composition for treating or preventing senile dementia, the active ingredients of which are prepared from raw medicinal materials comprising 20-50 parts by weight of Epimedium, 15-50 parts by weight of Poria, 15-50 parts by weight of Acanthopanax and 6-15 parts by weight of Anemarrhenae Rhizoma, preferably from traditional Chinese medicinal materials comprising 20-30 parts by weight of Epimedium, 20-30 parts by weight of Poria, 25-50 parts by weight of Acanthopanax, and 10-15 parts by weight of Anemarrhenae Rhizoma, more preferably from traditional Chinese medicinal materials comprising 30 parts by weight of Epimedium, 30 parts by weight of Poria, 25 parts by weight of Acanthopanax and 15 parts by weight of Anemarrhenae Rhizoma.

In the above traditional Chinese medicinal materials, Poria may be replaced by Poria cum Radix Pini or Polyporus; and Acanthopanax may be replaced by Acanthopanacis Cortex (Acanthopanax gracilistylus W. W.Smith) or Acanthopanacis Senticosi Folium (Acanthopanax senticosus (Rupr.et Maxim) Harms).

In a still further aspect, the present disclosure provides a process for preparing said pharmaceutical compositions in which:

said Poria can be processed by the following steps of extracting said weight parts of Poria with water 2-3 times each for 1-3 hours wherein the first extraction is carried out with water that is 6-10 times the weight of Poria; and the second and third extractions each are carried out with water that is 4-8 times the weight of Poria; filtering the resulting extract solution and concentrating it into a dry extract under reduced pressure; preferably said Poria is processed by the following steps of extracting said weight parts of Poria with water 3 times each for 1 hour wherein the first extraction is carried out with water that is 8 times the weight of Poria; and the second and third extractions each are carried out with water that is 6 times the weight of Poria; filtering the resulting extract solution and concentrating it into a dry extract under reduced pressure;

said Epimedium can be processed by the following steps of extracting said weight parts of Epimedium with 30-70% ethanol solution 2-3 times each for 1-3 hours, wherein the first extraction is carried out with 30-70% ethanol solution that is 7-16 times the weight of Epimedium; and the second and third extractions each are carried out with 30-70% ethanol solution that is 4-12 times the weight of Epimedium; filtering the resulting extract solution and recovering ethanol under reduced pressure followed by concentrating it into a dry extract; preferably said Epimedium is processed by the following steps of extracting said weight parts of Epimedium with 50% ethanol solution 3 times each for 1 hour, wherein the first extraction is carried out with 50% ethanol solution that is 9 times the weight of Epimedium; the second extraction is carried out with 50% ethanol solution that is 7 times the weight of Epimedium and the third extraction is carried out with 50% ethanol solution that is 5 times the weight of Epimedium; filtering the resulting extract solution and recovering ethanol under reduced pressure followed by concentrating it into a dry extract;

said Acanthopanax can be processed by the following steps of extracting said weight parts of Acanthopanax with water 2-3 times each for 1-3 hours wherein the first extraction is carried out with water that is 6-10 times the weight of Acanthopanax; and the second and third extractions each are carried out with water that is 4-8 times the weight of Acanthopanax; filtering the resulting extract solution and concentrating it into a dry extract under reduced pressure; preferably said Acanthopanax is processed by the following steps of extracting said weight parts of Acanthopanax with water 3 times each for 1 hour wherein the first extraction is carried out with water that is 8 times the weight of Acanthopanax; and the second and third extractions each are carried out with water that is 6 times the weight of Acanthopanax; filtering the resulting extract solution and concentrating it into a dry extract under reduced pressure; and said Anemarrhenae Rhizoma can be processed by the following steps of placing said weight parts of Anemarrhenae Rhizoma into water that is 6-10 times the weight of Anemarrhenae Rhizoma, heating the water until it boils and then decocting Anemarrhenae Rhizoma for 2-4 hours, removing and keeping the supernatant liquid, repeating the above process on the resulting residue again, and then filtering the combined extract solution followed by concentrating it into a dry extract; preferably said Anemarrhenae Rhizoma is processed by the following steps of placing said weight parts of Anemarrhenae Rhizoma into water that is 6 times the weight of Anemarrhenae Rhizoma, heating the water until it boils and then decocting Anemarrhenae Rhizoma for 2 hours, removing and keeping the supernatant liquid, repeating the extraction process on the resulting residue again, and then filtering the combined extract solution followed by concentrating it into a dry extract.

In one embodiment of the present disclosure, the pharmaceutical composition comprising Epimedium and Poria is formed by uniformly mixing the above dried Epimedium extract and above dried Poria extract. In one embodiment of the present disclosure, the pharmaceutical composition comprising Epimedium, Poria and Acanthopanax is formed by uniformly mixing the above dried Epimedium extract, above dried Poria extract and above dried Acanthopanax extract. In one embodiment of the present disclosure, the pharmaceutical composition comprising Epimedium, Poria, Acanthopanax and Anemarrhenae Rhizoma is formed by uniformly mixing the above dried Epimedium extract, above dried Poria extract, above dried Acanthopanax extract and above dried Anemarrhenae Rhizoma extract.

Moreover, the present disclosure provides a process for preparing said pharmaceutical compositions comprising Epimedium, Poria and Acanthopanax, which process comprises the following steps:

extracting said weight parts of Poria and said weight parts of Acanthopanax, separately or in combination, with water 2-3 times each for 1-3 hours, wherein the first extraction is carried out with water that is 6-10 times by weight; and the second and third extractions each are carried out with water that is 4-8 times by weight; filtering the resulting extract solution and concentrating it into a dry extract under reduced pressure; preferably extracting a mixture of said weight parts of Poria and said weight parts of Acanthopanax with water 3 times, each for 1 hour wherein the first extraction is carried out with water that is 8 times the weight of the mixture; and the second and third extractions each are carried out with water that is 6 times the weight of the mixture; filtering the resulting extract solution and concentrating it into a dry extract under reduced pressure;

extracting said weight parts of Epimedium with 30-70% ethanol solution 2-3 times each for 1-3 hours wherein the first extraction is carried out with 30-70% ethanol solution that is 7-16 times the weight of Epimedium; and the second and third extractions each are carried out with 30-70% ethanol solution that is 4-12 times the weight of Epimedium; filtering the resulting extract solution and recovering ethanol under reduced pressure followed by concentrating it into a dry extract; preferably extracting said weight parts of Epimedium with 50% ethanol solution 3 times each for 1 hour wherein the first extraction is carried out with 50% ethanol solution that is 9 times the weight of Epimedium; the second extraction is carried out with 50% ethanol solution that is 7 times the weight of Epimedium and the third extraction is carried out with 50% ethanol solution that is 5 times the weight of Epimedium; filtering the resulting extract solution and recovering ethanol under reduced pressure followed by concentrating it into a dry extract; and uniformly mixing above two resulting extracts.

Furthermore, the present disclosure provides a process for preparing said pharmaceutical compositions comprising Epimedium, Poria, Acanthopanax and Anemarrhenae Rhizoma, which process comprises the following steps:

extracting said weight parts of Poria and said weight parts of Acanthopanax, separately or in combination, with water 2-3 times each for 1-3 hours, wherein the first extraction is carried out with water that is 6-10 times by weight, and the second and third extractions each are carried out with water that is 4-8 times by weight; filtering the resulting extract solution and concentrating it into a dry extract under reduced pressure; preferably extracting a mixture of said weight parts of Poria and said weight parts of Acanthopanax with water 3 times, each for 1 hour wherein the first extraction is carried out with water that is 8 times the weight of the mixture; and the second and third extractions each are carried out with water that is 6 times the weight of the mixture; filtering the resulting extract solution and concentrating it into a dry extract under reduced pressure;

extracting said weight parts of Epimedium with 30-70% ethanol solution 2-3 times each for 1-3 hours wherein the first extraction is carried out with 30-70% ethanol solution that is 7-16 times the weight of Epimedium; and the second and third extractions each are carried out with 30-70% ethanol solution that is 4-12 times the weight of Epimedium; filtering the resulting extract solution and recovering ethanol under reduced pressure followed by concentrating it into a dry extract; preferably extracting said weight parts of Epimedium with 50% ethanol solution 3 times each for 1 hour wherein the first extraction is carried out with 50% ethanol solution that is 9 times the weight of Epimedium; the second extraction is carried out with 50% ethanol solution that is 7 times the weight of Epimedium and the third extraction is carried out with 50% ethanol solution that is 5 times the weight of Epimedium; filtering the resulting extract solution and recovering ethanol under reduced pressure followed by concentrating it into a dry extract;

placing said weight parts of Anemarrhenae Rhizoma into water that is 6-10 times the weight of Anemarrhenae Rhizoma, heating the water until it boils and then decocting Anemarrhenae Rhizoma for 2-4 hours, removing and keeping the supernatant liquid, repeating the extraction process on the resulting residue again, and then filtering the combined extract solution followed by concentrating it into a dry extract; preferably placing said weight parts of Anemarrhenae Rhizoma into water that is 6 times the weight of Anemarrhenae Rhizoma, heating the water until it boils and then decocting Anemarrhenae Rhizoma for 2 hours, removing and keeping the supernatant liquid, repeating the extraction process on the resulting residue again, and then filtering the combined extract solution followed by concentrating it into a dry extract; and uniformly mixing above three resulting extracts.

DETAILED DESCRIPTION

Example 1. Preparation of Pharmaceutical Composition

A. Extract from Epimedium (Pharmaceutical Composition A)

3 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out 50% ethanol solution that was 5 times the weight of Epimedium. The resulting extract solution was filtered and then concentrated into a dry extract under reduced pressure.

B. Extract from Poria (Pharmaceutical Composition B)

3 Kg of Poria was extracted with water 3 times each for 1 hour. The first extraction was carried out with water that was 8 times the weight of Poria, the second and third extractions each were carried out with water that was 6 times the weight of Poria. The resulting extract solution was filtered and then concentrated into a dry extract under reduced pressure.

C. Extract from Acanthopanax (Pharmaceutical Composition C)

3 Kg of Acanthopanax was extracted with water 3 times each for 1 hour. The first extraction was carried out with water that was 8 times the weight of Acanthopanax, the second and third extractions each were carried out with water that was 6 times the weight of Acanthopanax. The resulting extract solution was filtered and then concentrated into a dry extract under reduced pressure, yielding 0.12 kg.

D. Extract from Anemarrhenae Rhizoma (Pharmaceutical Composition D)

3 Kg of Anemarrhenae Rhizoma was added to water that was 6 times the weight of Anemarrhenae Rhizoma, the water was heated to boiling and Anemarrhenae Rhizoma was decocted for 2 hours. After that, the supernatant liquid was removed and kept, and the above process was repeated on the resulting residue again. The resulting extract solutions were combined and filtered and then concentrated into a dry extract under reduced pressure.

Preparation of Pharmaceutical Composition E consisting of 20 parts by weight of Epimendium and 50 parts by weight of Poria 5 Kg of Poria was extracted with water 3 times each for 1 hour. The first extraction was carried out with water that was 8 times the weight of Poria, the second and third extractions each were carried out with water that was 6 times the weight of Poria. The resulting extract solution was filtered and then concentrated into a dry extract under reduced pressure. 2 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out 50% ethanol solution that was 5 times the weight of Epimedium. The resulting extract solution was filtered and then concentrated into a dry extract under reduced pressure. The above two resulting extracts were mixed uniformly.

Preparation of Pharmaceutical Composition F consisting of 40 parts by weight of Epimendium and 55 parts by weight of Poria 1.1 Kg of Poria was extracted with water 3 times each for 1 hour. The first extraction was carried out with water that was 8 times the weight of Poria, the second and third extractions each were carried out with water that was 6 times the weight of Poria, respectively. The resulting extract solution was filtered and then concentrated into a dry extract under reduced pressure. 0.8 Kg of Epimendium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out 50% ethanol solution that was 5 times the weight of Epimedium. The resulting extract solution was filtered and then concentrated into a dry extract under reduced pressure. The above two resulting extracts were mixed uniformly.

Preparation of Pharmaceutical Composition F' consisting of 40 parts by weight of Epimendium and 55 parts by weight of Poria 1.1 Kg of Poria was extracted with water 2 times each for 3 hour. The first extraction was carried out with water that was 6 times the weight of Poria, the second extraction was carried out with water that was 4 times the weight of Poria. The resulting extract solution was filtered and then concentrated into a dry extract under reduced pressure. 1 Kg of Epimendium was extracted with 70% ethanol solution 2 times each for 1 hour. The first extraction was carried out with 70% ethanol solution that was 7 times the weight of Epimedium and the second extraction was carried out with 70% ethanol solution that was 4 times the weight of Epimedium. The resulting extract solution was filtered and then concentrated into a dry extract under reduced pressure. The above two resulting extracts were mixed uniformly.

Preparation of Pharmaceutical Composition G consisting of 50 parts by weight of Epimendium and 15 parts by weight of Poria 0.3 Kg of Poria was extracted with water 3 times each for 1 hour. The first extraction was carried out with water that was 8 times the weight of Poria, and the second and third extractions each were carried out with water that was 6 times the weight of Poria. The resulting extract solution was filtered and then concentrated into a dry extract under reduced pressure. 1 Kg of Epimendium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered and ethanol was recovered under reduced pressure followed by concentrating it into a dry extract. The above two resulting extracts were mixed uniformly.

Preparation Of Pharmaceutical Composition G' consisting of 50 parts by weight of Epimendium and 15 parts by weight of Poria 0.3 Kg of Poria was extracted with water 2 times each for 3 hours. The first extraction was carried out with water that was 10 times the weight of Poria and the second extractions was carried out with water that was 8 times the weight of Poria. The resulting extract solution was filtered and then concentrated into a dry extract under reduced pressure. 1 Kg of Epimendium was extracted with 30% ethanol solution 2 times each for 3 hours. The first extraction was carried out with 30% ethanol solution that was 16 times the weight of Epimendium and the second extraction was carried out with 30% ethanol solution that was 12 times the weight of Epimendium. The resulting extract solution was filtered and then concentrated into a dry extract under reduced pressure after recovering ethanol. The above two resulting extracts were mixed uniformly.

Preparation of Pharmaceutical Composition H Consisting of 50 Parts by Weight of Epimendium, 15 Parts by Weight of Poria and 10 Parts by Weight of Acanthopanax 1 Kg of Acanthopanax was extracted with water 3 times each for 1 hour. The first extraction was carried out with water that was 8 times the weight of Acanthopanax and the second and third extractions each were carried out with water that was 6 times the weight of Acanthopanax. The resulting extract solution was filtered and then concentrated into a dry extract under reduced pressure. 1.5 Kg of Poria was extracted with water 3 times each for 1 hour. The first extraction was carried out with water that was 8 times the weight of Poria and the second and third extractions each were carried out with water that was 6 times the weight of Poria. The resulting extract solution was filtered and then concentrated into a dry extract under reduced pressure. 5 Kg of Epimendium was extracted with 50% ethanol solution 3 times each for 1 hour. The first extraction was carried out with 50% ethanol solution that was 9 times the weight of Epimendium, the second extraction was carried out with 50% ethanol solution that was 7 times the weight of Epimendium and the third extraction was carried out with 50% ethanol solution that was 5 times the weight of Epimendium. The resulting extract solution was filtered, ethanol was recovered from the solution under reduced pressure and then the solution was concentrated into a dry extract. The above resulting three extracts were mixed uniformly.

Preparation of Pharmaceutical Composition H' consisting of 50 parts by weight of Epimendium, 15 parts by weight of Poria and 10 parts by weight of Acanthopanax 1 Kg of Acanthopanax was extracted with water 2 times each for 1 hour. The first extraction was carried out with water that was 6 times the weight of Acanthopanax and the second and third extractions each were carried out with water that was 4 times the weight of Acanthopanax. The resulting extract solution was filtered and then concentrated into a dry extract under reduced pressure. 1.5 Kg of Poria was extracted with water 2 times each for 3 hours. The first extraction was carried out with water that was 6 times the weight of Poria and the second extraction was carried out with water that was 4 times the weight of Poria. The resulting extract solution was filtered and then concentrated into a dry extract under reduced pressure. 5 Kg of Epimendium was extracted with 70% ethanol solution 2 times each for 1 hour. The first extraction was carried out with 70% ethanol solution that was 7 times the weight of Epimendium and the second extraction was carried out with 70% ethanol solution that was 4 times the weight of Epimendium. The resulting extract solution was filtered, ethanol was recovered from the solution under reduced pressure and then the solution was concentrated into a dry extract. The above resulting three extracts were mixed uniformly.

Preparation of Pharmaceutical Composition I consisting of 25 parts by weight of Epimendium, 45 parts by weight of Poria and 25 parts by weight of Acanthopanax A mixture of 9 kg of Poria and 5 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 5 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium and the third extraction was carried out with 50% ethanol solution that was 5 times the weight of Epimedium. The resulting extract solution was filtered, ethanol was recovered from the solution under reduced pressure and then the solution was concentrated into a dry extract. The above resulting two extracts were mixed uniformly.

Preparation of Pharmaceutical Composition J consisting of 30 parts by weight of Epimendium, 30 parts by weight of Poria and 35 parts by weight of Acanthopanax A mixture of 3 kg of Poria and 3.5 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 3 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium and the third extraction was carried out with 50% ethanol solution that was 5 times the weight of Epimedium. The resulting extract solution was filtered, ethanol was recovered from the solution under reduced pressure and then the solution was concentrated into a dry extract. The above resulting two extracts were mixed uniformly.

Preparation of Pharmaceutical Composition K consisting of 20 parts by weight of Epimendium, 40 parts by weight of Poria and 55 parts by weight of Acanthopanax A mixture of 0.8 kg of Poria and 1.1 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 0.4 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium and the third extraction was carried out with 50% ethanol solution that was 5 times the weight of Epimedium. The resulting extract solution was filtered, ethanol was recovered from the solution under reduced pressure and then the solution was concentrated into a dry extract. The above resulting two extracts were mixed uniformly.

Preparation of Pharmaceutical Composition L consisting of 20 parts by weight of Epimendium, 55 parts by weight of Poria and 20 parts by weight of Acanthopanax A mixture of 1.1 kg of Poria and 0.4 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 0.4 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium and the third extraction was carried out with 50% ethanol solution that was 5 times the weight of Epimedium. The resulting extract solution was filtered, ethanol was recovered from the solution under reduced pressure and then the solution was concentrated into a dry extract. The above resulting two extracts were mixed uniformly.

Preparation of Pharmaceutical Composition L' consisting of 20 parts by weight of Epimendium, 55 parts by weight of Poria and 20 parts by weight of Acanthopanax A mixture of 1.1 kg of Poria and 0.4 kg of Acanthopanax was extracted 2 times each for 3 hours. The first extraction was carried out with water that was 10 times the weight of the mixture and the second extraction was carried out with water that was 8 times the weight of the mixture. The resulting extract solution was filtered and then concentrated into a dry extract under reduced pressure. 0.4 kg of Epimedium was extracted with 30% ethanol solution 2 times each for 3 hours. The first extraction was carried out with 30% ethanol solution that was 16 times the weight of Epimedium, the second and third extractions each were carried out with 30% ethanol solution that was 12 times the weight of Epimedium. The resulting extract solution was filtered, ethanol was recovered from the solution under reduced pressure and then the solution was concentrated into a dry extract. The above resulting two extracts were mixed uniformly.

Preparation of Pharmaceutical Composition M consisting of 50 parts by weight of Epimendium, 15 parts by weight of Poria, 15 parts by weight of Acanthopanax and 15 parts by weight of Anemarrhenae Rhizoma A mixture of 3 kg of Poria and 3 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 10 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered, ethanol was recovered from the solution under reduced pressure and then the solution was concentrated into a dry extract. 3 Kg of Anemarrhenae Rhizoma was added to water that was 6 times the weight of Anemarrhenae Rhizoma, the water was heated to boiling and Anemarrhenae Rhizoma was decocted for 2 hours. After that the supernatant liquid was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition M' consisting of 50 parts by weight of Epimendium, 15 parts by weight of Poria, 15 parts by weight of Acanthopanax and 15 parts by weight of Anemarrhenae Rhizoma A mixture of said parts by weight of Poria and said parts by weight of Acanthopanax was extracted 3 times each for 1 hour. The first extraction was carried out with water that was 6 times the weight of the mixture and the second and third extractions each were carried out with water that was 4 times the weight of the mixture. The resulting extract solution was filtered and then concentrated into a dry extract under reduced pressure. Epimedium in above parts by weight was extracted with 30% ethanol solution 3 times each for 3 hours. The first extraction was carried out with 30% ethanol solution that was 16 times the weight of Epimedium, the second and third extractions each were carried out with 30% ethanol solution that was 12 times the weight of Epimedium. The resulting extract solution was filtered, ethanol was recovered from the solution under reduced pressure and then the solution was concentrated into a dry extract. Anemarrhenae Rhizoma in said parts by weight was added to water that was 6 times the weight of Anemarrhenae Rhizoma, the water was heated to boiling and Anemarrhenae Rhizoma was decocted for 2 hours. After that the supernatant was taken, the above process was repeated on the resulting residue again. Then the combined extract solution was filtered and concentrated into a dry extract under reduced pressure. The above resulting three extracts were mixed uniformly.

Preparation of Pharmaceutical Composition N consisting of 25 parts by weight of Epimendium, 30 parts by weight of Poria, 30 parts by weight of Acanthopanax and 10 parts by weight of Anemarrhenae Rhizoma A mixture of 6 kg of Poria and 6 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 5 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered, ethanol was recovered from the solution under reduced pressure and then the solution was concentrated into a dry extract. 2 Kg of Anemarrhenae Rhizoma was added to water that was 6 times the weight of Anemarrhenae Rhizoma, the water was heated to boiling and Anemarrhenae Rhizoma was decocted for 2 hours. After that the supernatant was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition 0 consisting of 30 parts by weight of Epimendium, 30 parts by weight of Poria, 25 parts by weight of Acanthopanax and 15 parts by weight of Anemarrhenae Rhizoma A mixture of 6 kg of Poria and 5 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 6 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered, ethanol was recovered from the solution under reduced pressure and then the solution was concentrated into a dry extract. 3 Kg of Anemarrhenae Rhizoma was added to water that was 6 times the weight of Anemarrhenae Rhizoma, the water was heated to boiling and Anemarrhenae Rhizoma was decocted for 2 hours. After that the supernatant was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition P consisting of 20 parts by weight of Epimendium, 20 parts by weight of Poria, 50 parts by weight of Acanthopanax and 12 parts by weight of Anemarrhenae Rhizoma A mixture of 2 kg of Poria and 5 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 2 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered, ethanol was recovered from the solution under reduced pressure and then the solution was concentrated into a dry extract. 1.2 Kg of Anemarrhenae Rhizoma was added to water that was 6 times the weight of Anemarrhenae Rhizoma, the water was heated to boiling and Anemarrhenae Rhizoma was decocted for 2 hours. After that the supernatant was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition Q consisting of 20 parts by weight of Epimendium, 50 parts by weight of Poria, 24 parts by weight of Acanthopanax and 6 parts by weight of Anemarrhenae Rhizoma A mixture of 5 kg of Poria and 2.4 kg of Acanthopanax was extracted 3 times each for 1 hour. The first extraction was carried out with water that was 8 times the weight of the mixture and the second and third extractions each were carried out with water that was 6 times the weight of the mixture. The resulting extract solution was filtered and then concentrated into a dry extract under reduced pressure. 2.0 Kg of Epimedium was extracted with 50% ethanol solution 3 times each for 1 hour. The first extraction was carried out with 50% ethanol solution that was 9 times the weight of Epimedium, the second extraction was carried out with 50% ethanol solution that was 7 times the weight of Epimedium, and the third extraction was carried out with 50% ethanol solution that was 5 times the weight of Epimedium. The resulting extract solution was filtered, ethanol was recovered from the solution under reduced pressure and then the solution was concentrated into a dry extract. 0.6 Kg of Anemarrhenae Rhizoma was added to water that was 6 times the weight of Anemarrhenae Rhizoma, the water was heated to boiling and Anemarrhenae Rhizoma was decocted for 2 hours. After that the supernatant was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition Q' consisting of 20 parts by weight of Epimendium, 50 parts by weight of Poria, 24 parts by weight of Acanthopanax and 6 parts by weight of Anemarrhenae Rhizoma A mixture of 5 kg of Poria and 2.4 kg of Acanthopanax was extracted 2 times each for 3 hours. The first extraction was carried out with water that was 10 times the weight of the mixture and the second extraction was carried out with water that was 8 times the weight of the mixture. The resulting extract solution was filtered and then concentrated into a dry extract under reduced pressure. 2.0 Kg of Epimedium was extracted with 70% ethanol solution 2 times each for 1 hour. The first extraction was carried out with 70% ethanol solution that was 7 times the weight of Epimedium and the second extraction was carried out with 70% ethanol solution that was 4 times the weight of Epimedium. The resulting extract solution was filtered, ethanol was recovered from the solution under reduced pressure and then the solution was concentrated into a dry extract. 0.6 Kg of Anemarrhenae Rhizoma was added to water that was 10 times the weight of Anemarrhenae Rhizoma, the water was heated to boiling and Anemarrhenae Rhizoma was decocted for 4 hours. After that the supernatant was removed and kept, and the above process was repeated on the resulting residue again. Then the combined extract solution was filtered and concentrated into a dry extract under reduced pressure. The above resulting three extracts were mixed uniformly.

Preparation of Pharmaceutical Composition R

The preparation process was the same as that of Pharmaceutical Composition J with the exception that Poria was replaced by Poria cum Radix Pini.

Preparation of Pharmaceutical Composition S

The preparation process was the same as that of Pharmaceutical Composition J with the exception that Poria was replaced by Polyporus.

Preparation of Pharmaceutical Composition T

The preparation process was the same as that of Pharmaceutical Composition J with the exception that Acanthopanax was replaced by Acanthopanacis Cortex.

Preparation of Pharmaceutical Composition U

The preparation process was the same as that of Pharmaceutical Composition J with the exception that Acanthopanax was replaced by Acanthopanacis Senticosi Folium.

As stated above, the present disclosure provides a pharmaceutical composition with a simple formulation, which may be used for treating or preventing senile dementia with definite curative effects.

Example 2. Effect On Learning and Memory in Rats Using Scopolamine-Induced Model 1. Materials Materials: Morris water maze device available from Tai Meng Technology Co. LTD, Chengdu City, China, DT-200 jump platform available from Tai Meng Technology Co. LTD, Chengdu City, China, Scopolamine Hydrobromide injection (Scop) available from Hua Yida Medical Technology Co. LTD, Wuhan City, China, and Donepezil Hydrochloride available from Eisai China Inc., China, specification: 5 mg, batch No. 120829A were used.

Animals: SD Male rats, available from Da Shuo Biological Technology Co. LTD, Chengdu City, China, were used.

2. Testing Method

Animal Grouping and Administration

Rats were randomly divided into Normal control group, Scop Model group, Positive control group (Donepezil, 1.17 mg/kg) and Experimental group (administered with a pharmaceutical composition of Example 1 in an amount of 11.08g raw medicinal materials per kg body weight). Before experiments, rats were fed by intragastric administration for 2 weeks. The normal control group and the model group were fed the same volume of distilled water. On day 9, rats were trained in the pool of Morris 2 times per day. On day 14, rats were subjected to do Morris water Maze and jump platform testing.

Model establishment and learning and memory test

On experiment day, rats were intragastrically administered. 30 Minutes later, they were administered with scopolamine hydrobromide (HBr) by intraperitoneal injections (2 mg·kg$^{-1}$ for two days and then 1 mg·kg$^{-1}$ on day 3). 20 Minutes later, rats were subjected to Morris water Maze testing. The normal control group was intraperitoneally injected with the same volume of saline. Their swimming performance was tracked and recorded by a camera. The travel path, time spent and speed of movement of rats in 90 s were recorded by a computer automatically, and the swimming distance and escape latency for finding the platform were calculated. Jump platform experiment: rats were trained on day one, and subjected to testing on day 2. 20 Minutes before testing, rats were intraperitoneally injected with scopolamine HBr in 5 mg·kg$^{-1}$. The first step down latency (SDL) and escape latency (the time required to escape from electric shock, EL) of rats were recorded.

3. Results

Effect on Morris water Maze tests of rats using Scopolamine induced Dysmnesia Model

TABLE 1

Effect on Morris water maze test ($\bar{x} \pm s$)

| Groups | Number of animals (n) | Escape latency(s) | Distance (cm) |
|---|---|---|---|
| Normal control | 10 | 18.86 ± 6.03** | 540.46 ± 100.24** |
| Model control | 10 | 49.63 ± 9.15 | 2173.42 ± 388.11 |
| Positive control | 10 | 37.27 ± 9.46** | 1647.50 ± 286.35** |
| Composition A | 10 | 41.69 ± 9.13 | 1897.60 ± 337.12 |
| Composition B | 10 | 41.42 ± 10.80 | 1896.44 ± 298.22 |
| Composition C | 10 | 42.82 ± 10.06 | 1875.75 ± 272.57 |
| Composition D | 10 | 42.27 ± 8.60 | 1868.96 ± 293.34 |
| Composition E | 10 | 40.65 ± 8.87* | 1794.70 ± 333.61* |
| Composition F | 10 | 40.51 ± 8.62* | 1826.32 ± 251.11* |
| Composition G | 10 | 40.10 ± 8.71* | 1792.36 ± 279.36* |
| Composition J | 10 | 35.23 ± 8.20** | 1644.08 ± 342.53** |
| Composition O | 10 | 34.66 ± 10.37** | 1641.50 ± 226.13** |

Compared with the model control group, *P < 0.05 and **P < 0.01.

The data in Table 1 clearly demonstrate that in the Morris water maze test, the performance of Scop induced dysmnesia model rats were improved by using pharmaceutical compositions A, B, C and D although not obvious (P>0.05). Different improvements were achieved when using all other pharmaceutical compositions, in which the use of composition J and composition O produced the most obvious improvement, and the difference was statistically significant (P<0.01).

Effect on rats jump platform test using Scopolamine induced Dysmnesia Model

TABLE 2

Effect on rats in jump platform test ($\bar{x} \pm s$)

| Groups | Number of animals (n) | SDL(s) | EL(s) |
|---|---|---|---|
| Normal control | 10 | 100.60 ± 14.26** | 59.41 ± 11.80** |
| Model control | 10 | 16.04 ± 7.22 | 130.63 ± 19.46 |
| Positive control | 10 | 28.67 ± 11.70** | 109.17 ± 11.17** |
| Composition A | 10 | 22.23 ± 7.69 | 116.13 ± 15.71 |
| Composition B | 10 | 20.85 ± 7.00 | 115.96 ± 13.43 |
| Composition C | 10 | 21.93 ± 6.72 | 119.95 ± 12.52 |
| Composition D | 10 | 22.76 ± 7.60 | 119.81 ± 13.66 |
| Composition E | 10 | 24.09 ± 5.97* | 113.70 ± 13.00* |
| Composition F | 10 | 24.61 ± 7.37* | 113.50 ± 12.59* |
| Composition G | 10 | 24.26 ± 6.94* | 113.52 ± 11.72* |
| Composition J | 10 | 27.71 ± 6.04** | 108.98 ± 13.41** |
| Composition O | 10 | 27.83 ± 5.67** | 108.67 ± 12.50** |

Compared with the model control group, *P < 0.05 and **P < 0.01.

The data in Table 2 clearly demonstrate that in the rats jump platform test, the performance of Scop induced dysmnesia model rats were improved by using pharmaceutical compositions A, B, C and D although not obvious (P>0.05). Different improvements were achieved when using all other pharmaceutical compositions, in which composition J and composition O produced the most obvious improvement, and the difference was statistically significant (P<0.01).

Example 3. Effect on Learning and memory of APPswe Transgenic Mice

1. Materials

Material: Morris water maze device available from Tai Meng Technology Co. LTD, Chengdu City, China, Homemade Object Recognition device; and Donepezil Hydrochloride available from Eisai China Inc., Specification: 5 mg, batch number 120829A, were used.

Animals: APPswe transgenic mice in 5 months, available from Nanjing animal model institute, were used.

2. Testing Method

Animal grouping and Administration

APPswe transgenic mice, half male and half female, were randomly divided into four groups: model control group, positive control group (donepezil, 1.67 mg·kg⁻), experimental group (administered with a pharmaceutical composition of Example 1 in an amount of 15.83 g raw medicinal materials per kg body weight). APPswe mice with the same background and age (available from Nanjing animal model institute, without expression of human presenilin and amyloid precursor protein, and without suffering senile dementia) were used as the normal control group. Each group was given the corresponding drugs by intragastric administration and the normal control group and model control group were given distilled water of the same volume, once a day for 30 days.

Morris water Maze test

On day 25 to day 29 after administration, mice in each group were trained for water maze, 2 times per day. 1 Hour after the last administration, the location of the platform remained unchanged and the escape latency and swimming path of the mice for finding the platform were recorded by an automatic camera system, in which the maximum latency time was set as 120 s. The recording automatically stopped after 120 s.

Object recognition test

In light of animal's habit of "loving the new and loathing the old", a homemade object recognition device was used for detection of animal learning and memory ability. The first day is the adaptation phase, during which mice were put in carton with good lighting and allowed to adapt to it and freely move for about 10 min. The second day is the familiar phase, during which two same toys were put in a box and mice were placed in the box for 10 min Exploration time to each object was recorded. The third day is the recognition phase, during which another object was placed in the box to replace one toy and exploration time to each object was recorded. The resolution index to the new toy in each group was calculated according to the following formula:

Resolution index=(the time to the new object−the time to the old object)/(the time to the new object+the time to the old object).

3. Results

1) Effect on APPswe mice water Maze test

TABLE 3

Effect on Morris water maze test ($\bar{x} \pm s$)

| Groups | Number of animals (n) | Escape latency(s) | Distance (cm) |
|---|---|---|---|
| Normal control | 10 | 50.50 ± 9.42** | 479.24 ± 94.26** |
| Model control | 10 | 86.14 ± 14.30 | 982.81 ± 160.96 |
| Positive control | 10 | 68.23 ± 12.00** | 783.50 ± 145.12** |
| Composition A | 10 | 73.07 ± 14.43 | 840.02 ± 152.86 |
| Composition B | 10 | 74.16 ± 13.58 | 847.45 ± 157.24 |
| Composition C | 10 | 74.70 ± 10.82 | 842.36 ± 149.22 |
| Composition D | 10 | 74.01 ± 12.56 | 843.20 ± 148.06 |
| Composition H | 10 | 69.54 ± 13.39* | 790.90 ± 146.33* |
| Composition I | 10 | 66.70 ± 14.48** | 759.20 ± 162.61** |
| Composition J | 10 | 64.16 ± 13.16** | 751.08 ± 175.17** |
| Composition K | 10 | 65.08 ± 12.40** | 755.08 ± 146.47** |
| Composition L | 10 | 68.93 ± 16.66* | 792.65 ± 192.96* |
| Composition R | 10 | 68.50 ± 15.32* | 786.33 ± 154.35* |
| Composition S | 10 | 68.87 ± 14.35* | 795.12 ± 142.72* |
| Composition T | 10 | 68.92 ± 13.03* | 786.96 ± 164.43* |
| Composition U | 10 | 69.34 ± 12.34* | 803.46 ± 172.33* |
| Composition M | 10 | 67.58 ± 15.21* | 776.10 ± 183.60* |
| Composition N | 10 | 63.98 ± 11.06** | 744.57 ± 157.55** |
| Composition O | 10 | 61.56 ± 15.11** | 736.28 ± 149.50** |
| Composition P | 10 | 62.26 ± 11.83** | 747.78 ± 144.17** |
| Composition Q | 10 | 68.77 ± 13.66* | 782.94 ± 156.02* |

Compared with the model control group, *P < 0.05 and **P < 0.01.

The data in Table 3 clearly demonstrate that in the Morris water Maze test, the performance of Appswe mice were improved by using pharmaceutical compositions A, B, C and D although not obvious (P>0.05). Different improvements were achieved when using all other pharmaceutical compositions, and compared with the model control group, the difference was statistically significant (P<0.01-0.15).

2) Effect on APPswe mice object recognition test

TABLE 4

Effect on object recognition test ($\bar{x} \pm s$)

| Groups | Number of animals (n) | Resolution index |
|---|---|---|
| Normal control | 10 | 0.304 ± 0.131** |
| Model control | 10 | 0.105 ± 0.044 |
| Positive control | 10 | 0.176 ± 0.051** |
| Composition A | 10 | 0.147 ± 0.053 |

TABLE 4-continued

Effect on object recognition test ($\bar{x} \pm s$)

| Groups | Number of animals (n) | Resolution index |
|---|---|---|
| Composition B | 10 | 0.146 ± 0.061 |
| Composition C | 10 | 0.152 ± 0.058 |
| Composition D | 10 | 0.147 ± 0.049 |
| Composition H | 10 | 0.174 ± 0.074* |
| Composition I | 10 | 0.188 ± 0.064** |
| Composition J | 10 | 0.197 ± 0.078** |
| Composition K | 10 | 0.184 ± 0.055** |
| Composition L | 10 | 0.175 ± 0.067* |
| Composition R | 10 | 0.169 ± 0.074* |
| Composition S | 10 | 0.166 ± 0.056* |
| Composition T | 10 | 0.168 ± 0.072* |
| Composition U | 10 | 0.168 ± 0.080* |
| Composition M | 10 | 0.175 ± 0.075* |
| Composition N | 10 | 0.196 ± 0.045** |
| Composition O | 10 | 0.201 ± 0.055** |
| Composition P | 10 | 0.197 ± 0.062** |
| Composition Q | 10 | 0.174 ± 0.079* |

Compared with the model control group, *P < 0.05 and **P < 0.01.

The data in Table 4 clearly demonstrate that the exploration time of Appswe mice was improved by using pharmaceutical compositions A, B, C and D although not obvious (P>0.05). Different improvements on exploration time of Appswe mice were achieved when using all other pharmaceutical compositions, and compared with model control group, the difference was statistically significant (P<0.01~0.15).

Example 4. Effect on Learning and Memory in Mice Using Scopolamine-Induced Model 1. Materials Materials: Morris water maze device available from Tai Meng Technology Co. LTD, Chengdu City, China, DT-200 jump platform available from Tai Meng Technology Co. LTD, Chengdu City, China, scopolamine HBr injection (Scop) available from Hua Yida Medical Technology Co. LTD, Wuhan City, China, and Donepezil Hydrochloride available from Eisai China Inc., China, specification: 5 mg, batch No. 120829A were used.

Animals: KM mice, available from Da Shuo Biological Technology Co. LTD, Chengdu City, China, were used.

2. Testing method

Animal Grouping and Administration

Mice were randomly divided into Normal control group, Scop Model group, Positive control group (Donepezil, 1.67 mg/kg) and Experimental group (administered with a pharmaceutical composition of Example 1, in a dosage of 31.66 g raw medicinal materials/kg for composition A, B and C, and in a high dosage of 31.66 g raw medicinal materials/kg, a middle dosage of 15.83 g raw medicinal materials/kg and a low dosage of 7.92 g raw medicinal materials/kg for composition J). Before experiments, mice of experimental group were fed by intragastric administration of a pharmaceutical composition for 2 weeks, while the normal control group and the model group were fed the same volume of distilled water. On day 9, mice were trained in the pool of Morris, 2 times per day. On day 14, mice were subjected to Morris water Maze testing.

Model establishment and learning and memory test

On experiment day, mice were fed by intragastric administration. 30 Minutes later, they were administered with Scop in a dosage of 3 mg·kg$^{-1}$ via intraperitoneal injection. 20 Minutes later, the mice were subjected to Morris water Maze testing. The normal control group was intraperitoneally injected with the same volume of saline. The swimming performance of mice were tracked and recorded by a camera. The travel path, time spent and speed of movement of mice in 300 s were recorded by a computer automatically. The maximum latency was set as 300 s. The recording stopped after 300 s. The escape latency and swimming distance for looking for the platform were recorded.

3. Results

TABLE 5

Effect on Mice in Morris water Maze test ($\bar{x} \pm s$)

| Groups | Number of animals (n) | Escape latency(s) | Swimming Distance (cm) |
|---|---|---|---|
| Normal control | 10 | 92.09 ± 10.74** | 2052.09 ± 232.41** |
| Model control | 10 | 176.54 ± 18.74 | 3646.54 ± 574.35 |
| Positive control | 10 | 141.42 ± 25.85** | 2738.70 ± 534.75** |
| Composition A | 10 | 154.88 ± 28.38 | 2920.88 ± 601.84* |
| Composition B | 10 | 157.59 ± 25.91 | 3104.59 ± 396.84* |
| Composition C | 10 | 154.28 ± 22.05* | 3148.28 ± 589.34 |
| Composition J (high dosage) | 10 | 133.55 ± 28.98** | 2453.55 ± 511.18** |
| Composition J (middle dosage) | 10 | 136.95 ± 28.74** | 2576.95 ± 527.11** |
| Composition J (low dosage) | 10 | 149.26 ± 24.82* | 2989.66 ± 530.04* |

Compared with the model control group, *P < 0.05 and **P < 0.01.

The data in Table 5 clearly demonstrate that in the Morris water maze test, various compositions produced different improvements on the performance of Scop induced dysmnesia model mice, in which composition J in the high, middle and low dosage produced the most obvious improvement, and the difference was significant statistically (P<0.01 0.05).

Example 5. Clinical Trial Study

1. Selection of subjects:
1.1 Diagnostic Criteria:

The criteria of NINCDS-ADRDA-R were used, including core diagnostic criteria A, supportive features B and exclusion criteria as shown below.

TABLE 6

Core diagnostic criteria, supportive features and exclusion criteria

Core diagnostic criteria
A. Presence of an early and significant episodic memory impairment that includes the following features:
1. Gradual and progressive change in memory function reported by patients or informants over more than 6 months
2. Objective evidence of significantly impaired episodic memory on testing: this generally consists of recall deficit that does not improve significantly or does not normalise with clue or recognition testing and after effective encoding of previously control information
3. The episodic memory impairment can be isolated or associated with other cognitive changes at the onset of AD or as AD advances
Supportive features
B. Presence of medial temporal lobe atrophy (MTA)
Volume loss of hippocampi, entorhinal cortex, amygdala evidenced on MRI with qualitative ratings using visual scoring (referenced to well characterized population with age norms) or quantitative volumetry of regions of interest (referenced to well characterized population with age norms)

TABLE 6-continued

Core diagnostic criteria, supportive features and exclusion criteria

C. Abnormal cerebrospinal fluid biomarker
Low amyloid β$_{1-42}$ concentrations, increased total tau concentrations, or increased phospho-tau concentrations, or combinations of the three
Other well validated markers to be discovered in the future
D. Specific pattern on functional neuroimaging with PET
Reduced glucose metabolism in bilateral temporal parietal regions
Other well validated ligands, including those that foreseeably will emerge such as Pittsburg compound B or FDDNP
E. Proven AD autosomal dominant mutation within the immediate family
Exclusion criteria
History
Sudden onset
Early occurrence of the following symptoms: gait disturbances, seizures, behavioural changes
Clinical features
Focal neurological features including hemiparesis. sensory loss, visual field deficits
Early extrapyramidal signs
Other medical disorders severe enough to account for memory and related symptoms
Non-AD dementia
Major depression
Cerebrovascular disease
Toxic and metabolic abnormalities, all of which may require specific investigations
MRI FLAIR or T2 signal abnormalities in the medial temporal lobe that are consistent with infectious or vascular insults 1.2. Inclusion Criteria (1) 60 Years of age or older, male or female.
(2) Meeting the diagnostic criteria of AD, and also meeting the above criteria of TCM syndromes.
(3) Degree of education above the primary school.
(4) Without stroke history.
(5) Hachiski ischemic score (HIS) of below 4 points.
(6) Clear and definite Brain MR (with brain atrophy and without other cranial lesions).
(7) MMSE score: 9~24 scores for middle school or higher; and 9~20 scores for primary school; CDR score: mild to moderate patients with 1 or 2 scores.
(8) Patients who have not taken any medicines for treating dementia for more than 1 week.

1.3 Exclusion criteria:

(1) Patients who are subjected to severe cardiac or cerebral vascular diseases, severe liver or kidney disease, or pulmonary infection.
(2) Patients who can't cooperate with the treatment or are subjected to drug allergy.
(3) Patients who are subjected to severe depression (as demonstrated by depression table).
(4) Patients who are subjected to vascular dementia (VD), Parkinson disease dementia (PDD), dementia with Lewy bodies (DLB), frontotemporal dementia (FTD) or the like.
(5) Severe AD patients or patients who are subjected to severe neurological impairment so that inspection cannot be completed.
(6) Patients who are taking Aricept, Memantine, Huperzine A, Nimoldipine, Ginseng, Ginkgo folium, saffron or the like currently or within 1 week.

1.4 Removal or failure criteria:

(1) Patients who have poor medication compliance or fail to take medicine for more than 1 month.
(2) Patients who are subjected to serious diseases and have to stay in hospital.
(3) Patients who do not meet the inclusion criteria but have been mistakenly included or who meet the inclusion criteria but have failed to comply with the prescribed medication.

1.5 Termination criteria:

(1) Patients who suffer other severe disease in the course of the trial.
(2) Patients with serious adverse events during the trial or patients whose treatments have to stop according to the doctor's judgment.
(3) Patients who cannot continue to be treated due to non-therapeutic reasons or drop out voluntarily.

2. Preparation and administration of trial medicines

350 Kg of Acanthopanax, 300kg of Epimedium and 300 kg of Poria were extracted as above, thereby affording 26 kg of extract from Acanthopanax and Poria and 54 kg of extract from Epimedium. The obtained extracts were pulverized, added with a proper amount of starch and dextrin, and then made into granules. After sterilization, the medicament was packaged in 8 g/bag. The medicament was administered in a dosage of one bag twice per day, morning and evening. The daily dosage of raw medicinal materials for adults was 30 g of Epimedium, 35 g of Acanthopanax and 30 g of Poria. The treatment cycle was 6 months.

3. Observation

The following observations were made on patients before enrollment and during the 6 months of treatment:
(1) ADAS-cog scale.
(2) MMSE scale.
(3) Activities of daily living scale (ADL).
(4) Clinical dementia rating scale (CDR).
(5) Neuropsychiatric Inventory scale (NPI).

4. Standard for evaluation of curative effect

Main index
(1) Cognitive function assessment: comparison of MMSE, ADAS-cog, and CDR scores with baseline levels.
(2) Overall situation: CDR overall assessment.
Secondary index
(1) Assessment of activities of daily living activities: change of ADL scores before and after treatment.
(2) Evaluation of mental behavior: comparative analysis on change of the neuropsychiatric inventory scale (NPI) scores before and after treatment.

5. Study results

TABLE 7

Part of the clinical data

| | | | Before administration | | | | | After 6 months' administration | | | | |
|---|---|---|---|---|---|---|---|---|---|---|---|---|
| No. | Gender | Age | MMSE | ADAS-cog | ADL | NPI | CDR | MMSE | ADAS-cog | ADL | NPI | CDR |
| 1 | M | 78 | 20 | 29 | 28 | 1 | 1 | 21 | 25 | 20 | 0 | 0.5 |
| 2 | F | 80 | 12 | 36 | 31 | 5 | 1 | 17 | 30 | 22 | 0 | 1 |
| 3 | F | 76 | 20 | 38 | 39 | 3 | 1 | 19 | 27 | 24 | 0 | 1 |
| 4 | M | 73 | 19 | 22 | 26 | 0 | 1 | 27 | 13 | 20 | 0 | 0.5 |
| 5 | M | 80 | 9 | 45 | 27 | 6 | 2 | 11 | 41 | 31 | 7 | 2 |
| 6 | F | 73 | 13 | 49 | 37 | 0 | 2 | 20 | 41 | 33 | 0 | 2 |

TABLE 7-continued

Part of the clinical data

| | | | Before administration | | | | | After 6 months' administration | | | | |
|---|---|---|---|---|---|---|---|---|---|---|---|---|
| No. | Gender | Age | MMSE | ADAS-cog | ADL | NPI | CDR | MMSE | ADAS-cog | ADL | NPI | CDR |
| 7 | M | 81 | 14 | 38 | 42 | 5 | 2 | 24 | 26 | 38 | 1 | 1 |
| 8 | M | 74 | 21 | 26 | 24 | 0 | 1 | 27 | 17 | 20 | 0 | 0.5 |
| 9 | F | 74 | 12 | 54 | 40 | 11 | 2 | 13 | 38 | 30 | 0 | 1 |
| 10 | F | 76 | 15 | 37 | 24 | 0 | 1 | 21 | 24 | 24 | 0 | 1 |
| 11 | F | 64 | 23 | 24 | 24 | 0 | 1 | 28 | 15 | 20 | 0 | 0.5 |
| 12 | F | 79 | 19 | 32 | 27 | 0 | 1 | 26 | 18 | 23 | 0 | 0.5 |
| 13 | F | 78 | 10 | 55 | 33 | 3 | 2 | 17 | 35 | 27 | 0 | 1 |
| 14 | M | 77 | 13 | 45 | 41 | 2 | 2 | 18 | 35 | 29 | 1 | 1 |
| 15 | F | 84 | 13 | 43 | 36 | 2 | 2 | 17 | 39 | 32 | 0 | 1 |
| 16 | F | 72 | 21 | 26 | 27 | 2 | 1 | 25 | 15 | 20 | 0 | 0.5 |

The above clinical data of table 7 were statistically analyzed and the results were as follows:

TABLE 8-1

Effect on MMSE, ADAS-cog and CDR scores ($\bar{x} \pm s$, n = 16)

| | MMSE | | ADAS-cog | | CDR | |
|---|---|---|---|---|---|---|
| Group | Before administration | After administration | Before administration | After administration | Before administration | After administration |
| Experimental group | 15.88 ± 4.46 | 20.69 ± 5.13** | 37.44 ± 10.48 | 27.44 ± 9.90** | 1.44 ± 0.51 | 0.94 ± 0.48** |

Compared with the corresponding values before administration,
**P < 0.01

TABLE 8-2

Rating of severity of disease based on CDR scores

| | Number of improved cases (improvement rate) | |
|---|---|---|
| CDR scores | Before administration | After 6 months' administration |
| Moderate | 7 patients | 5 (71.4%) |
| Mild | 9 patients | 6 (66.7%) |

The data in Table 8-1 demonstrate that the medication treatment for 6 months significantly improved MMSE, ADAS cog and CDR scores, and as compared with the baseline scores before administration, the differences were statistical significant (P<0.01), indicating that the medicament significantly improved cognitive function in AD patients. The data in Table 8-2 demonstrate that, according to the CDR scores, 5 of 7 patients of moderate AD after taking medicine for 6 months turned to mild, showing an improvement rate of 71.4% and 6 of 9 patients of mild AD after taking medicine for 6 months turned to suspected dementia, showing an improvement rate of 66.7%.

TABLE 9

Effect on NPI and ADL scores

| | NPI | | ADL | |
|---|---|---|---|---|
| Group | Before administration | After administration | Before administration | After administration |
| Experimental group | 2.50 ± 3.03 | 0.56 ± 1.75* | 31.62 ± 6.60 | 25.81 ± 5.73** |

Compared with the corresponding values before administration, *P < 0.05, **P < 0.01

The data in Table 9 clearly demonstrate that patients after taking medicines for 6 months had obviously improved NPI and ADL, and compared with the baseline scores before administration, the differences were statistically significant (P <0.01-0.05), indicating that the medicament significantly improved nerve and mental conditions and daily life ability of AD patients.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., 1 to 5 includes 1, 1.5, 2, 2.75, 3, 3.80, 4, 5, etc.).

Furthermore, disclosure of a range includes disclosure of all subranges included within the broader range (e.g., 1 to 5 discloses 1 to 4, 1.5 to 4.5, 4 to 5, etc.).

Various embodiments of the invention have been described. These and other embodiments are within the scope of the following claims.

What is claimed is:

1. A pharmaceutical composition comprising active ingredients, wherein the active ingredients of the pharmaceutical composition are prepared from raw medicinal materials consisting of 20-50 parts by weight of Epimedii Folium and 15-55 parts by weight of Poria or Poria cum Radix Pini.

2. A pharmaceutical composition comprising active ingredients, wherein the active ingredients of the pharmaceutical composition are prepared from raw medicinal materials consisting of 20-50 parts by weight of Epimedii Folium, 15-55 parts by weight of Poria or Poria cum Radix Pini and 10-55 parts by weight of Acanthopanax.

3. The pharmaceutical composition as claimed in claim 2, wherein the active ingredients of the pharmaceutical composition are prepared from raw medicinal materials consisting of 20-30 parts by weight of Epimedii Folium, 20-45 parts by weight of Poria or Poria cum Radix Pini and 20-55 parts by weight of Acanthopanax.

4. The pharmaceutical composition as claimed in claim 3, wherein the active ingredients of the pharmaceutical composition are prepared from raw medicinal materials consisting of 30 parts by weight of Epimedii Folium, 30 parts by weight of Poria or Poria cum Radix Pini, and 35 parts by weight of Acanthopanax.

5. A pharmaceutical composition comprising active ingredients, wherein the active ingredients of the pharmaceutical composition are prepared from raw medicinal materials consisting of 20-50 parts by weight of Epimedii Folium, 15-50 parts by weight of Poria or Poria cum Radix Pini, 15-50 parts by weight of Acanthopanax and 6-15 parts by weight of Anemarrhenae Rhizoma.

6. The pharmaceutical composition as claimed in claim 5, wherein the active ingredients of the pharmaceutical composition are prepared from raw medicinal materials consisting of 20-30 parts by weight of Epimedii Folium, 20-30 parts by weight of Poria or Poria cum Radix Pini, 25-50 parts by weight of Acanthopanax, and 10-15 parts by weight of Anemarrhenae Rhizoma.

7. The pharmaceutical composition as claimed in claim 6, wherein the active ingredients of the pharmaceutical composition are prepared from raw medicinal materials consisting of 30 parts by weight of Epimedii Folium, 30 parts by weight of Poria or Poria cum Radix Pini, 25 parts by weight of Acanthopanax and 15 parts by weight of Anemarrhenae Rhizoma.

8. The pharmaceutical composition as claimed in claim 1, wherein said Poria is processed by:
   extracting said weight parts of Poria with water 2-3 times each for 1-3 hours, to generate a resulting extract solution, wherein a first extraction of Poria is carried out with water that is 6-10 times the weight of Poria, and a second extraction of Poria is carried out with water that is 4-8 times the weight of Poria; and
   filtering the resulting extract solution and concentrating the resulting extract solution into a dry extract under reduced pressure.

9. The pharmaceutical composition as claimed in claim 1, wherein said Epimedii Folium is processed by:
   extracting said weight parts of Epimedii Folium with 30-70% ethanol solution 2-3 times each for 1-3 hours, to produce a resulting extract solution, wherein a first extraction of Epimedii Folium is carried out with 30-70% ethanol solution that is 7-16 times the weight of Epimedii Folium, and a second extraction of Epimedii Folium is carried out with 30-70% ethanol solution that is 4-12 times the weight of Epimedii Folium; and
   filtering the resulting extract solution and recovering ethanol under reduced pressure followed by concentrating the resulting extract solution into a dry extract.

10. The pharmaceutical composition as claimed in claim 2, wherein said Acanthopanax is processed by:
   extracting said weight parts of Acanthopanax with water 2-3 times each for 1-3 hours, to generate a resulting extract solution, wherein a first extraction of Acanthopanax is carried out with water that is 6-10 times the weight of Acanthopanax, and a second extraction of Acanthopanax is carried out with water that is 4-8 times the weight of Acanthopanax; and
   filtering the resulting extract solution and concentrating the resulting extract solution into a dry extract under reduced pressure.

11. The pharmaceutical composition as claimed in claim 5, wherein said Anemarrhenae Rhizoma is processed by:
   placing said weight parts of Anemarrhenae Rhizoma into water that is 6-10 times the weight of Anemarrhenae Rhizoma,
   heating the water until the water and Anemarrhenae Rhizoma boils and then decocting Anemarrhenae Rhizoma for 2-4 hours,
   removing and keeping the supernatant liquid,
   repeating the heating and removing on the resulting residue again to generate a combined extract solution, and then
   filtering the combined extract solution followed by concentrating the combined extract solution into a dry extract.

* * * * *